(12) United States Patent
Lemonnier

(10) Patent No.: US 6,240,768 B1
(45) Date of Patent: Jun. 5, 2001

(54) SAMPLING METHOD AND SAMPLING APPARATUS FOR THE MICROBIOLOGICAL ANALYSIS OF AIR

(75) Inventor: Jean Lemonnier, Paris (FR)

(73) Assignee: Millipore S.A., Paris (FR)

( * ) Notice: Subject to any disclaimer, the term of this patent is extended or adjusted under 35 U.S.C. 154(b) by 0 days.

(21) Appl. No.: 09/310,516

(22) Filed: May 12, 1999

(30) Foreign Application Priority Data

Jun. 10, 1998 (FR) .................................................. 98 07298

(51) Int. Cl.[7] .............................. G01N 1/24; C12M 1/26; C12M 1/34
(52) U.S. Cl. ........................................ 73/28.05; 73/863.22
(58) Field of Search ............................... 73/28.04, 28.05, 73/863.21, 863.22

(56) References Cited

U.S. PATENT DOCUMENTS 3,922,905   12/1975   Roth ...................................... 73/28.04

FOREIGN PATENT DOCUMENTS 2 732 692   10/1996   (FR) .
1 441 576   7/1976   (GB) .................................... 73/28.05
2 224 118   4/1990   (GB) .................................... 73/28.05

*Primary Examiner*—Daniel S. Larkin
(74) *Attorney, Agent, or Firm*—John Dana Hubbard; Timothy J. King; Paul J. Cook

(57) ABSTRACT

A method and apparatus for sampling microorganisms from the air is disclosed. The speed at which the sample is placed on to a growth medium is controlled, such as by controlling the speed of the turbine of the device, so as to compensate for any drying of the medium that may have occurred by the amount of air hitting the surface over time. This enhances the ability of the medium to retain microorganisms present in the air even as the medium dries from the flow of air over its surface.

10 Claims, 3 Drawing Sheets

SAMPLING METHOD AND SAMPLING APPARATUS FOR THE MICROBIOLOGICAL ANALYSIS OF AIR

The invention relates to the microbiological analysis of air.

BACKGROUND OF THE INVENTION

It is known that, in order to effect such an analysis, use is generally made of a sampling apparatus for depositing microorganisms, such as bacteria, yeasts, or moulds, present in an air sample, on a layer of growth media in a receptacle, and that next this receptacle is put to incubate at the required temperature and for the required length of time to enable the deposited micro-organisms to develop in the form of colonies visible to the naked eye, so that they can be counted and identified.

SUMMARY OF THE INVENTION

The invention aims to make it possible to perform the operation of depositing microorganisms on the layer of growth media under conditions such that the colonies which are visible after incubation faithfully reflect the microorganism population of the sample being checked.

To this end, it is proposed a sampling method for the microbiological analysis of air including an operation of depositing microorganisms on a layer of growth media which is contained in a receptacle by sucking in air at the periphery of the receptacle in order to cause the air to pass through holes in a perforated wall with the same contour as that of the layer of growth media and disposed opposite this layer and concentrically with it, air which comes to strike the layer of growth media; characterized in that the operation of depositing microorganisms includes the operation of increasing the air suction rate in a predetermined fashion as a function of the volume of air already sucked in.

Increasing the suction rate amounts to increasing the mean speed at which the air strikes the layer of growth media.

This increase in speed, which is effected as a function of the volume of air already sucked in, makes it possible to compensate at least partially for the reduction in the ability of the layer of growth media to retain the microorganisms because of the drying of the layer of growth media at the place where it is struck by the air, drying which makes it harder and less adherent.

According to preferred features, having regard to the tests carried out by the inventor, the operation of depositing includes the operation of sucking in a first predetermined volume of air at a first predetermined constant rate and then sucking in a second predetermined volume of air at a second constant predetermined rate higher than the first predetermined rate.

Preferably, having regard to the characteristics of the growth media generally used for effecting an air analysis:
  the first predetermined volume of air is substantially five hundred liters; and/or
  the first predetermined flow rate is adapted so that the mean speed at which the growth media is struck by the jets of air is between 11 and 12 m/s and the second predetermined flow rate is adapted so that the mean striking speed is between 14.5 and 15.5 m/s.

The invention also relates, in a second aspect, to an apparatus suitable for implementing the method that has just been disclosed.

To this end, it proposes an apparatus having a sieve with a wall perforated with a multitude of holes, means for holding a removable receptacle containing a layer of growth media with a contour similar to that of the perforated wall in a predetermined position in which the layer of growth media is disposed opposite the perforated wall and concentrically with it, and means for sucking air at the periphery of the receptacle held in the predetermined position in order to cause to enter the apparatus, through the holes, air which strikes the layer of growth media; characterized in that the means for sucking air include means for increasing the air suction rate in a predetermined fashion as a function of the volume of air already sucked in.

According to preferred features for embodying this apparatus, the means for increasing the air suction rate include means for controlling the speed of rotation of a motor driving a suction turbine according to the number of revolutions already effected by this motor.

The disclosure of the invention will now be continued with a description of an example embodiment given below for illustration and nonlimitatively, with reference to the accompanying drawings.

IN THE DRAWINGS

FIG. 4 is a graph the variation in the mean speed at which the air strikes the layer of growth media as a function of the volume of air sucked in.

DETAILED DESCRIPTION OF THE INVENTION

Figure 1:
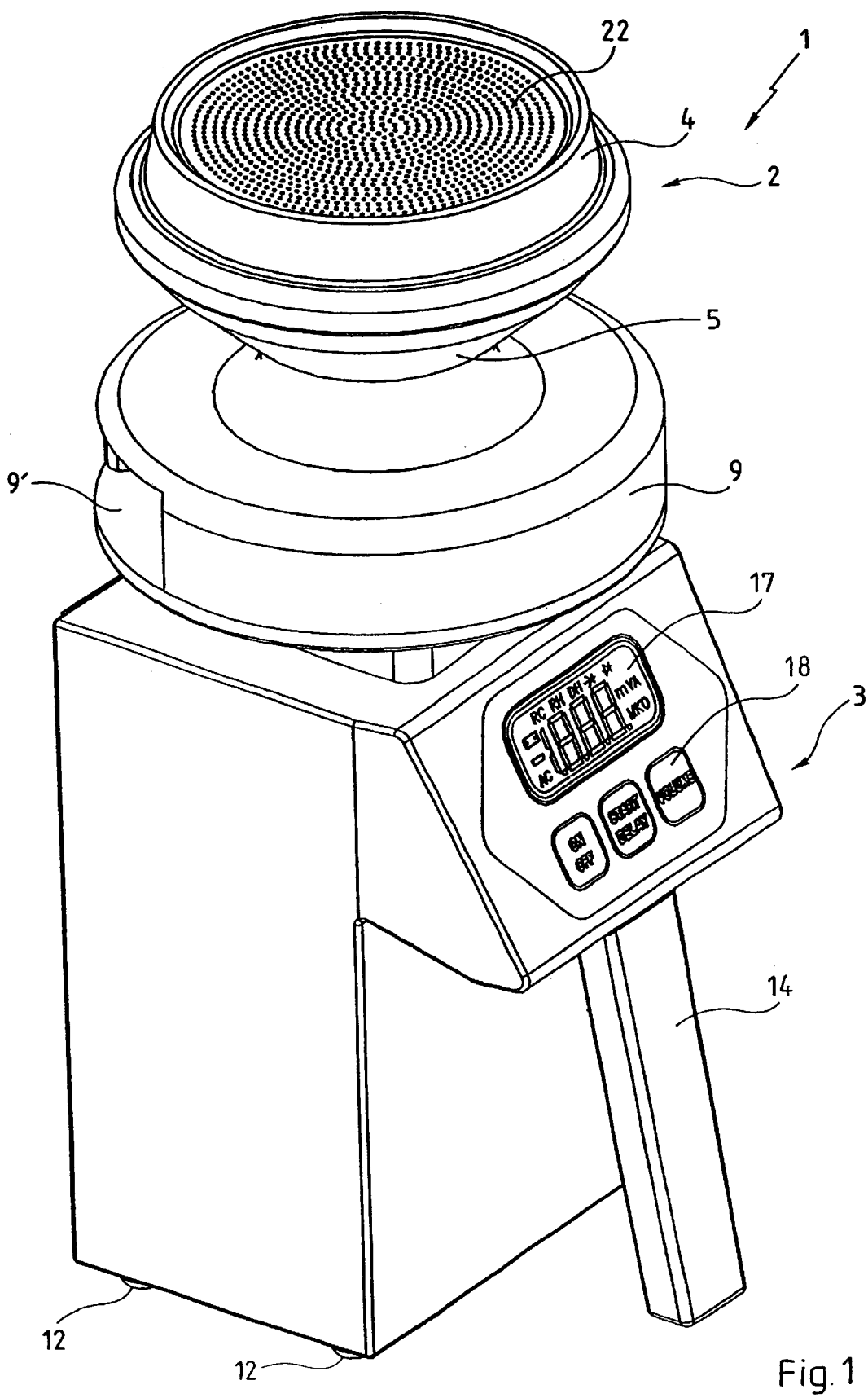
FIG. 1 is a perspective view of a first embodiment of the apparatus according to the present invention.
Figure 2:
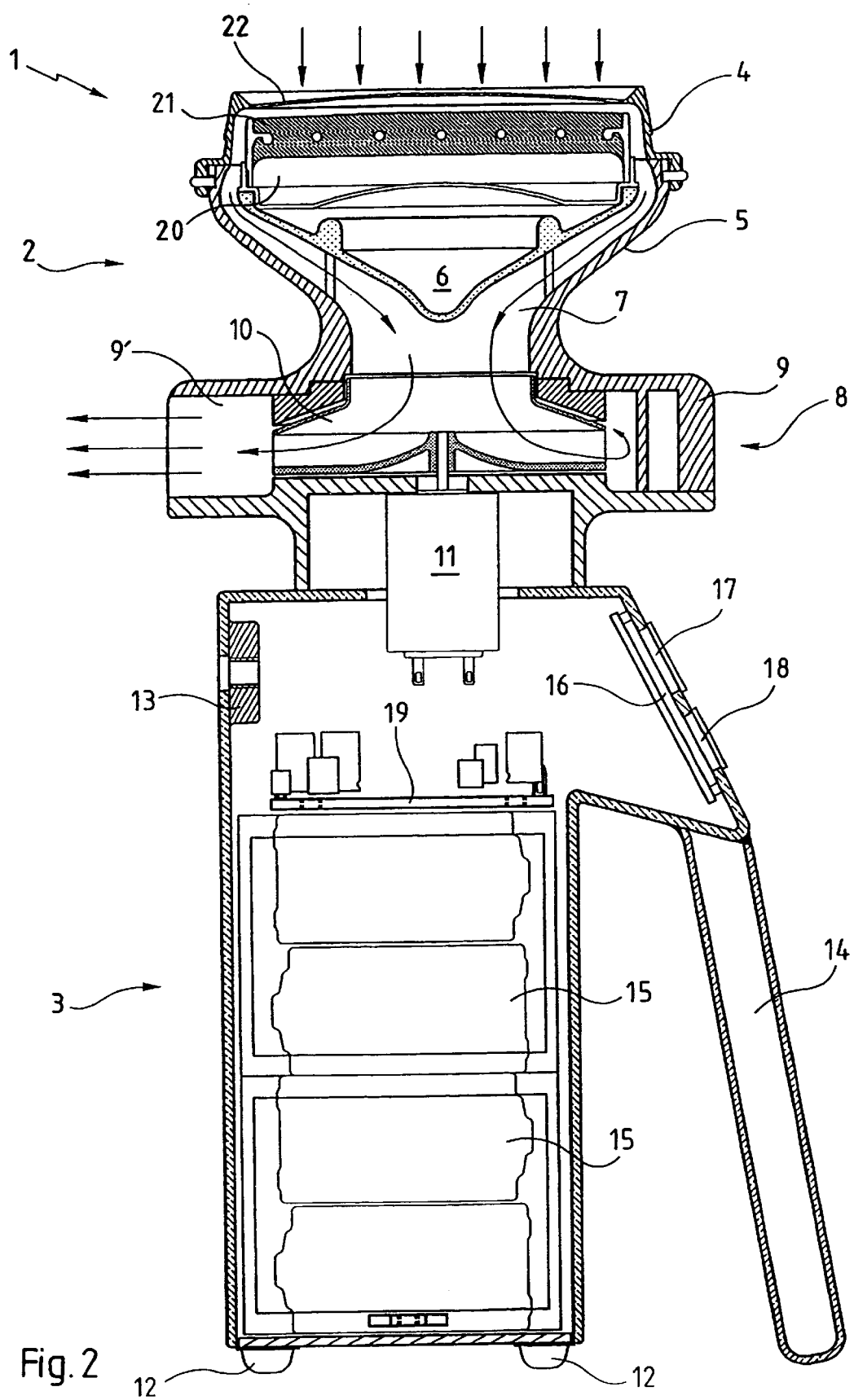
FIG. 2 is a view of FIG. 1 thereof in elevation and section.
Figure 3:
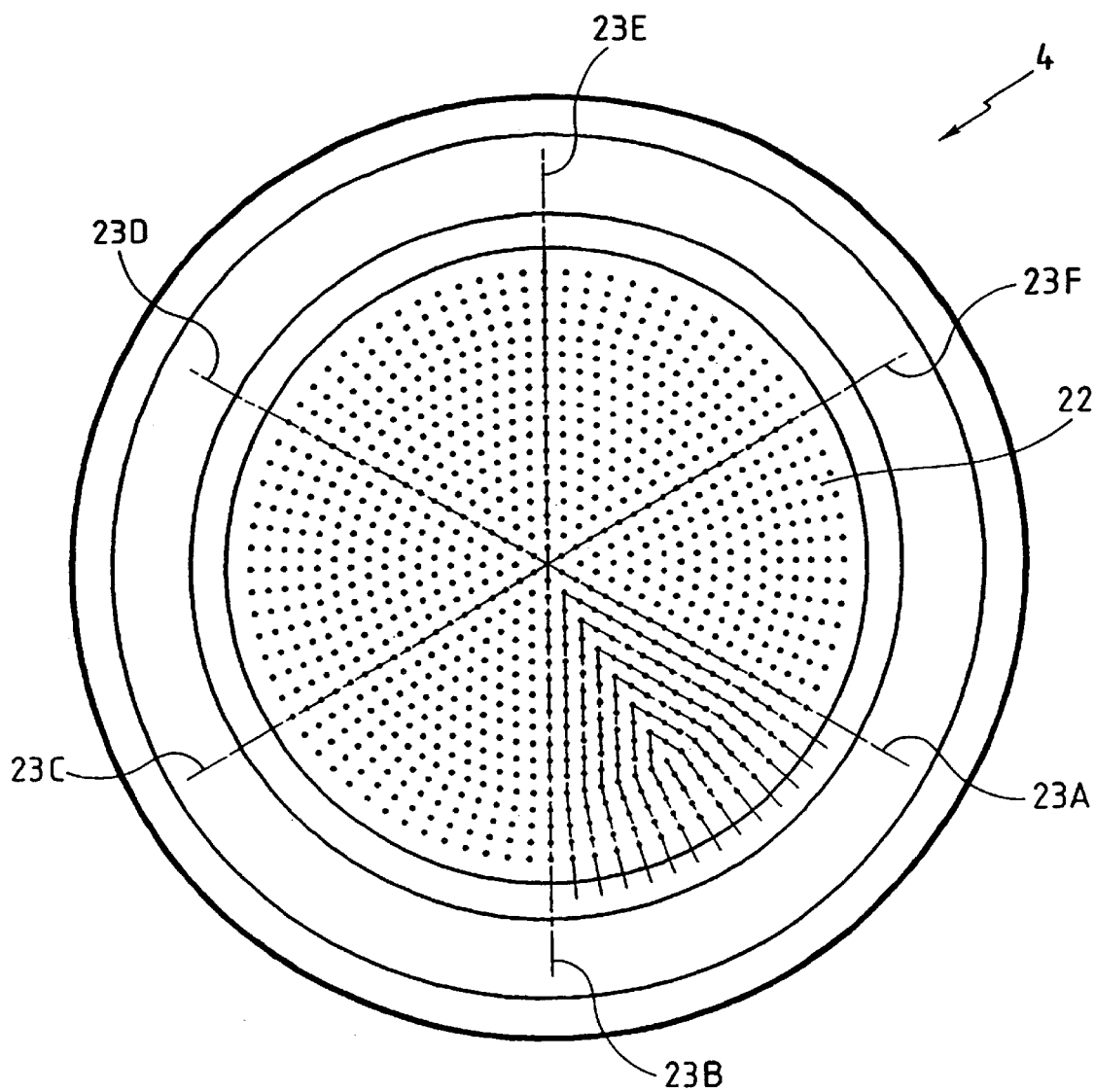
FIG. 3 is a plan view of an embodiment of the sieve included in the apparatus of the present invention.
Figure 4:
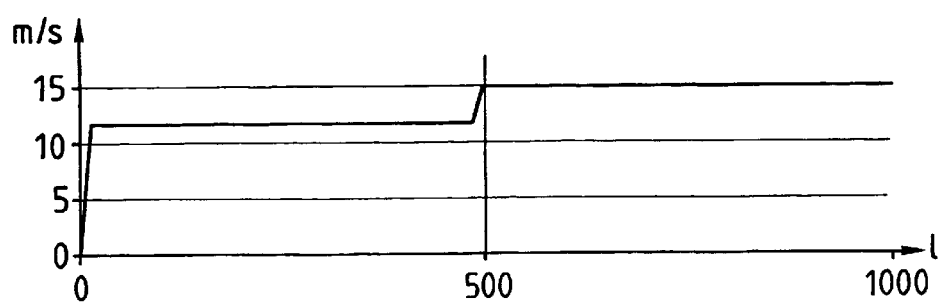

The apparatus 1 as illustrated has a sampling head 2 and a body 3.

The sampling head 2 has a sieve 4, an aerodynamic sleeve 5 on the end of which the sieve 4 is removably mounted, a defector 6 disposed in the sleeve 5 so that there is an air suction duct 7 between the deflector and the sleeve, and a turbine 8 having a stator 9 fixed to the sleeve 5 and a rotor 10 for sucking air into the duct 7 and for discharging it through the side discharge orifice 9'.

The rotor 10 of the turbine 8 is driven by an electric motor 11, which partially enters the body 3.

The body 3 serves in general terms to hold the apparatus 1 and to control the motor 11. The body 3 has externally, opposite the head 2, feet 12 by means of which the apparatus 1 can be placed vertically. The body mat also include a base 13 having a threaded hole for fixing the apparatus 1, for example horizontally, to a support, such as a conventional camera tripod, and a handle 14 for gripping the apparatus 1. The body 3 contains a set of electrical batteries 15, an electrical circuit 16 having a display 17 and a simplified keypad 18 disposed above the handle 14, as well as another electrical circuit 19, and a certain number of electrical conductors, not shown, serving to effect the necessary connections between the motor 11, the batteries 15, and the circuits 16 and 19.

The sampling head 2 is designed to receive a receptacle 20 containing a layer of growth media 21 with a similar contour to that of the perforated wall 22 of the sieve 4, and to hold this receptacle in the illustrated position in which the layer of growth media is disposed opposite the perforated wall 22 and concentrically with it. The selected growth media is preferably a self supported media, such as gelled media like agar, although other growth media may be used so long as it is incorporated into a self supporting structure, such as a pad or a sponge.

The receptacle 20 is more precisely held by virtue of notches (not illustrated) provided on the end of the aerodynamic sleeve 5, notches in each of which there is housed one of the lugs (not illustrated) which the receptacle 20 has projecting with respect to its lateral wall, the fitting of the base of the receptacle 20 (the part of the receptacle opposite to the surface of the layer of growth media which faces the perforated wall 22) in the deflector 6 serving to close off the latter. More details on the cooperation between the receptacle 20 and the sampling head 2 are given in the French patent application No 98-05166, to which reference can be made if desired.

It should be noted simply that the fact that the receptacle 20 and the sieve 4 are both mounted on the same support (the end of the sleeve 5) makes it possible to have a very precise positioning of the sieve with respect to the receptacle, and that the surface of the layer of growth media 21 which is opposite the perforated wall 22 is delimited at the time of manufacture (when the layer of growth media 21 is poured) by a film tensioned over the end surface of the annular wall which surrounds the layer of growth media 21, so that the geometry of this surface is particularly precise and repetitive from one receptacle 20 to another.

Because of the conformation of the side wall of the receptacle 20 and that of the sieve 4, the duct 7 also exists all around the receptacle 20 so that, when the rotor 10 rotates, there is a suction of air at the periphery of the receptacle 20 and therefore a suction of external air which enters the apparatus 1 though the multitude of holes in the perforated wall 22, as shown by the arrows in FIG. 2.

Whereas the surface of the layer of growth media 21 which faces the wall 22 is flat (it may however be very slightly curved because the film delimiting this surface at the time of manufacture adopts a small deflection when the growth media is poured), the wall 22 is curved in the direction in which it is concave on the side which faces the layer of growth media 21, here in a portion of a sphere, such as an arc, so that the separation between the wall 22 and the layer of growth media 21 increases from their periphery towards their center.

By virtue of this variable separation, the holes provided in the wall 22, which are particularly high in number, as can be seen in FIGS. 1 and 3, are all capable of being useful, that is to say of each creating a flow of air coming to strike the layer of growth media 21 in the form of a jet which encounters the latter at a sufficiently high speed for any microorganism present in the flow of air to be fixed on the layer of growth media by impaction and sufficiently low for the micro-organism to remain revivable.

As can be seen more particularly in FIG. 3, the holes in the perforated wall 22 are solely disposed in concentric circles as well as in six circular sectors delimited by the radii 23A to 23F, which are disposed at 600 to each other.

The holes in the first fourteen consecutive circles as from the center of each of the six sectors are disposed in a series of parallel chevrons whose apex is turned towards the center, so that there are six identical series of chevrons which are externally delimited respectively by the chevron formed by the radii 23A and 23B, by that formed by the radii 23B and 23C and so on.

As a result, for each series of chevrons, the apex of the one which is furthest towards the outside is situated on the hole which is exactly at the center of the perforated wall 22, the apex of the second chevron is on a hole in the second circle, and so on until the seventh and last chevron, whose apex is on the twelfth consecutive circle from the center.

From the fifteenth to the eighteenth and last circle, the number of holes remains the same as for the fourteenth circle, each of the holes in these circles being aligned on a radius, with a respective hole in the fourteenth circle.

As can be seen in FIG. 3 for the sector situated between the radii 23A and 238, where all the alignments of holes have been depicted, there are channels between these alignments, going as far as the periphery of the wall 22, the number of the channels being higher as the periphery of this wall is approached.

When the rotor 10 is driven in rotation, the jets of air existing between the wall 22 and the layer of growth media 21 are disposed in the same way as the holes in this wall, and there therefore exist, between the alignments of air jets, paths (corresponding to the above mentioned channels) by virtue of which the air can be discharged without obstacle to the peripheral suction channel 7, so that coexistence between the air entering the apparatus in the form of jets and that discharging at the periphery is achieved with a minimum degree of mutual interference.

It will be observed that the concentric circles in which the holes in the wall 22 are disposed are substantially equidistant, and it will be noted that this distance is around 2 mm, that the holes in the wall 22 all have substantially the same size, here, a diameter of around 0.5 mm, that the number of holes per unit surface area of the perforated wall is substantially uniform, here around twenty-five holes per $cm^2$, and that the total number of holes in the wall 22 is slightly less than one thousand holes.

Because the separation between the layer of growth media 21 and the perforated wall 22 has geometric characteristics which are repeated from one receptacle 20 to another, the air flow sucked in for each rotation of the rotor 10 remains the same, and consequently the speed at which the air strikes the layer of growth media 21 remains the same for the same speed of rotation of the rotor, and the volume of air sucked in remains the same for the same number of rotations effected by the rotor.

FIG. 4 shows how the mean speed at which the layer of growth media 21 is struck by the air jets is varied according to the volume already sucked in, that is to say here how the circuits 16 and 19 vary the speed of rotation of the motor 11 as a function of the number of rotations already effected by the latter.

At the start, the speed of rotation of the motor 11 is fixed so that the mean speed of the air through the holes in the wall 22 (the ratio between the total flow rate and the total surface area of the holes) is around 11.5 m/s and this speed is maintained constant until a volume of approximately five hundred liters has been sucked in, and the speed of rotation of the motor is then increased so that the mean speed is 15 m/s and this speed of rotation is maintained until the whole of the sample, that is to say one thousand liters (1 $m^3$), has been sucked in.

This variation in the speed of impaction on the growth media as a function of the volume already sucked in reduces the risk that the microorganisms may not be retained by the layer of growth media because the latter undergoes a certain degree of drying as the sample is taken at each place where the growth media is struck by an air jet, the increase in speed compensating for the increase in hardness and the reduction in adhesion due to the drying.

In variants which are not shown, the air suction rate (and therefore the mean speed at which the growth media is struck) is increased progressively rather than in stages or with more than two stages; the holes are distributed differently on the perforated wall 22, notably by providing a different number of concentric circles and radii delimiting sectors where the holes are distributed identically; and/or the increase in separation between the layer of growth media and the perforated wall is achieved differently, for example, with a perforated wall which is flat and a layer of growth media which is concave on the side which faces the perforated wall.

Numerous other variants are possible according to circumstances, and it should be stated in this regard that the invention is not limited to the examples described and depicted.

What I claim:

1. A method for conducting a microbiological analysis of air comprising depositing microorganisms on a layer of growth media which is contained in a receptacle; sucking in air at the periphery of the receptacle in order to cause the air to pass through holes in a perforated wall with the same contour as that of the layer of growth media and disposed opposite this layer and concentrically with this layer, air which comes to strike the layer of growth media; and increasing the air suction rate in a predetermined fashion as a function of the volume of air already sucked in.

2. The method of claim 1 wherein the operation of depositing includes the operation of sucking in a first predetermined volume of air at a first predetermined constant rate, and then sucking in a second predetermined volume of air at a second constant predetermined rate higher than the first predetermined rate.

3. The method of claim 1 wherein increasing the air suction rate occurs after about five hundred liters of air has been sucked in.

4. The method of claim 1 wherein the increasing in air suction rate is based upon two predetermined rates; a first predetermined rate is adapted so that the mean speed at which the growth media is struck by the air is between 11 and 12 m/s, and the second predetermined rate is adapted so that the mean striking speed is between 14.5 and 15.5 m/s.

5. An apparatus suitable for implementing the method of claim 1 comprising a sieve with a wall perforated with a multitude of holes; a holder for a removable receptacle containing a layer of growth media with a contour similar to that of the perforated wall in a predetermined position in which the layer of growth media is disposed opposite the perforated wall and concentrically with the wall, and a device for sucking air at the periphery of the receptacle held in the predetermined position in order to cause air to enter the apparatus through the holes, where the air strikes the layer of growth media; and wherein the device for sucking air include a means for increasing the air suction rate in a predetermined fashion as a function of the volume of air already sucked in.

6. The apparatus of claim 5 wherein the means for increasing the air suction rate is adapted to suck in a first predetermined volume of air at a first predetermined constant rate, and then to suck in a second predetermined volume of air at a second predetermined constant rate higher than the first predetermined rate.

7. The apparatus of claim 5 wherein the means for increasing the air suction rate, is adapted to suck in a first predetermined volume of air at a first predetermined constant rate, and then to suck in a second predetermined volume of air at a second predetermined constant rate higher than the first predetermined rate, and the first predetermined volume of air is about 500 liters of air being sucked in.

8. The apparatus of claim 5 wherein the means for increasing the air suction rate is adapted to suck in a first predetermined volume of air at a first predetermined constant rate, and then to suck in a second predetermined volume of air at a second predetermined constant rate higher than the first predetermined rate and the first predetermined constant rate is adapted so that the mean speed at which the growth media is struck by the air is between 11 and 12 m/s and the second predetermined rate is adapted so that the mean striking speed is between 14.5 and 15.5 m/s.

9. The apparatus of claim 5 wherein the means for increasing the air suction rate is a controller for the speed of rotation of a motor driving a suction turbine so as to vary the number of rotations in a given time effected by the motor.

10. A method for conducting the microbiological analysis of air comprising depositing microorganisms on a layer of growth media which is contained in a receptacle; sucking in air at the periphery of the receptacle in order to cause the air to pass through holes in a perforated wall with the same contour as that of the layer of growth media and disposed opposite this layer and concentrically with this layer, air which comes to strike the layer of growth media; wherein the operation of depositing includes the operation of sucking in a first predetermined volume of air at a first predetermined constant rate, and then sucking in a second predetermined volume of air at a second constant predetermined rate higher than the first predetermined rate, the first predetermined rate is adapted so that the mean speed at which the growth media is struck by the air is between 11 and 12 m/s, and the second predetermined rate is adapted so that the mean striking speed is between 14.5 and 15.5 m/s.

* * * * *